US012708344B2

(12) United States Patent
Pinkovich et al.

(10) Patent No.: US 12,708,344 B2
(45) Date of Patent: Aug. 18, 2026

(54) METHOD AND SYSTEM FOR ANALYZING ULTRASOUND SCENES TO PROVIDE NEEDLE GUIDANCE AND WARNINGS

(71) Applicant: GE Precision Healthcare LLC, Wauwatosa, WI (US)

(72) Inventors: Dani Pinkovich, Haifa (IL); Doron Shaked, Haifa (IL); Sagi Schein, Haifa (IL); Antonio Fabian Fermoso, Madrid (ES); Naomi Sato, Tokyo (JP); Ruth Bergman, Haifa (IL)

(73) Assignee: GE Precision Healthcare LLC, Waukesha, WI (US)

( * ) Notice: Subject to any disclaimer, the term of this patent is extended or adjusted under 35 U.S.C. 154(b) by 1375 days.

(21) Appl. No.: 16/574,360

(22) Filed: Sep. 18, 2019

(65) Prior Publication Data

US 2021/0077061 A1 Mar. 18, 2021

(51) Int. Cl.
*A61B 17/34* (2006.01)
*A61B 8/08* (2006.01)
(Continued)

(52) U.S. Cl.
CPC ............ *A61B 8/0841* (2013.01); *A61B 8/085* (2013.01); *A61B 17/3403* (2013.01); *A61B 8/461* (2013.01);
(Continued)

(58) Field of Classification Search
CPC ... A61B 8/0841; A61B 8/085; A61B 17/3403; A61B 2090/378; A61B 2017/3413; A61B 8/461
See application file for complete search history.

(56) References Cited

U.S. PATENT DOCUMENTS

2006/0184029 A1* 8/2006 Haim .................. A61B 8/0833 600/443
2009/0137907 A1* 5/2009 Takimoto .............. A61B 8/466 600/461
(Continued)

FOREIGN PATENT DOCUMENTS

WO WO2018157868 * 9/2018

OTHER PUBLICATIONS

F. Conversano, M. Peccarisi, P. Pisani, M. D. Paola, et. al. "Automatic ultrasound technique to measure angle of progression during labor." Ultrasound Obstetrics Gynecology, Wiley, vol. 50, No. 6, pp. 766-775, (Year: 2017).*

*Primary Examiner* — Amal Aly Farag
(74) *Attorney, Agent, or Firm* — McAndrews, Held & Malloy, Ltd.; Daniel Bissing; David Bates

(57) ABSTRACT

A system and method for analyzing ultrasound scenes to provide needle guidance and warnings is provided. The method includes acquiring, by an ultrasound system, an ultrasound image. The method includes segmenting, by at least one processor, the ultrasound image to identify a plurality of structures in the ultrasound image. The method includes highlighting, by the at least one processor, the plurality of structures in the ultrasound image to create a highlighted ultrasound image. The method includes presenting, by the at least one processor, the highlighted ultrasound image at a display system. The method includes determining, by the at least one processor, a distance between at least two of the plurality of structures in the ultrasound image. The method includes providing, by the at least one processor, a warning if the distance between the at least two of the plurality of structures in the ultrasound image is less than a threshold.

20 Claims, 5 Drawing Sheets

(51) Int. Cl.
*A61B 8/00* (2006.01)
*A61B 90/00* (2016.01)
*G16H 30/20* (2018.01)

(52) U.S. Cl.
CPC . *A61B 2017/3413* (2013.01); *A61B 2090/378* (2016.02); *G16H 30/20* (2018.01)

(56) References Cited

U.S. PATENT DOCUMENTS

2012/0029387 A1* 2/2012 Wei ........................ A61B 90/36 600/587
2013/0131501 A1* 5/2013 Blaivas ................ A61B 8/4455 600/424
2013/0323700 A1* 12/2013 Samosky ............... G09B 23/28 434/262
2016/0317119 A1* 11/2016 Tahmasebi Maraghoosh ............. A61B 8/085

* cited by examiner

METHOD AND SYSTEM FOR ANALYZING ULTRASOUND SCENES TO PROVIDE NEEDLE GUIDANCE AND WARNINGS

FIELD

Certain embodiments relate to ultrasound imaging. More specifically, certain embodiments relate to a method and system providing ultrasound scene analysis for needle guidance and warnings.

BACKGROUND

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

During an ultrasound-based regional anesthesia procedure, an anesthesiologist may operate both an ultrasound system and the insertion and navigation of a needle to its destination such that an appropriate amount of anesthetic medium may be administered to the destination (e.g., a designated nerve). Accordingly, the anesthesiologist may provide simultaneous visual attention to the ultrasound system display and the patient such that the anesthesiologist may track targets (e.g., the needle, the designated nerve, etc.) while navigating the needle around critical organs (e.g., vessels) to the destination. Interpretation of the ultrasound images during invasive procedures, such as regional anesthesia or catheterization, is critically important since actions due to wrong interpretation could result in waste of time, pain to the patient, and in some cases permanent damage.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for analyzing ultrasound scenes to provide needle guidance and warnings, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
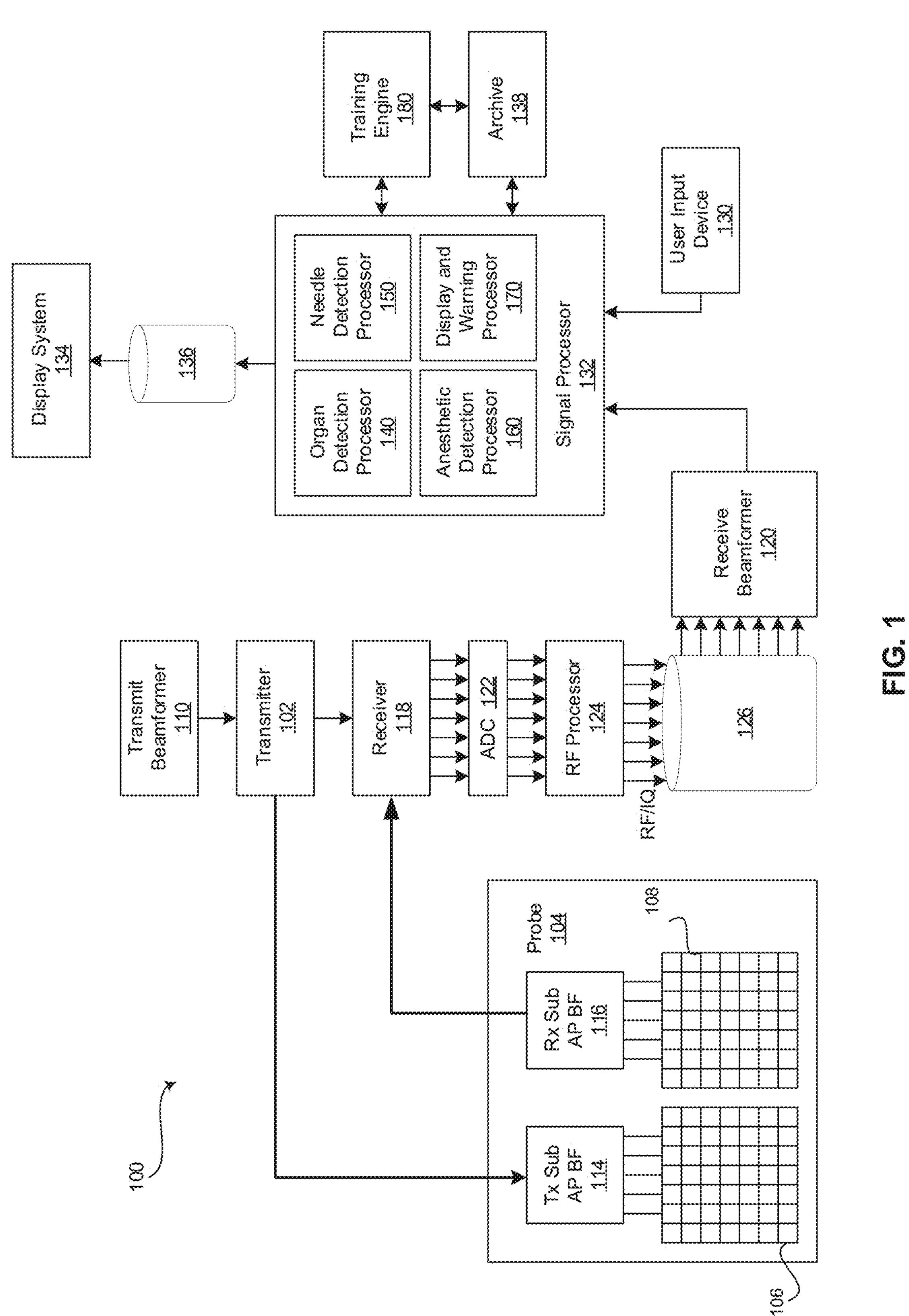
FIG. 1 is a block diagram of an exemplary ultrasound system that is operable to provide ultrasound scene analysis for needle guidance and warnings, in accordance with various embodiments.

Certain embodiments may be found in a method and system for analyzing ultrasound scenes to provide needle guidance and warnings. Various embodiments have the technical effect of dynamically identifying and highlighting biological (e.g., nerves and vessels) and/or artificial structures (e.g., a needle and anesthetic medium) in ultrasound images. Aspects of the present disclosure have the technical effect of providing needle guidance (e.g., trajectories overlaid on image), location-based warnings (e.g., audio, visual, and/or physical warnings), and/or other information (e.g., percentage of nerve covered by anesthetic medium) based on the location of biological and/or artificial structures identified and highlighted in ultrasound images.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to provide ultrasound scene analysis for needle guidance and warnings, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, an archive 138, and a training engine 180.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise an organ detection processor 140, a needle detection processor 150, an anesthetic detection processor 160, and a display and warning processor 170. The signal processor 132 may be capable of receiving input information from a user input device 130 and/or archive 138, generating an output displayable by a display system 134, and manipulating the output in response to input information from a user input device 130, among other things. The signal processor 132, organ detection processor 140, needle detection processor 150, anesthetic detection processor 160, and display and warning processor 170 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include an organ detection processor 140 that comprises suitable logic, circuitry, interfaces and/or code that may be operable to analyze acquired ultrasound images to identify and segment organs, such as nerves, vessels, or any suitable biological structures. The organ detection processor 140 may include artificial intelligence image analysis algorithms, one or more deep neural networks (e.g., a convolutional neural network) and/or may utilize any suitable form of artificial intelligence image analysis techniques or machine learning processing functionality configured to analyze acquired ultrasound images to identify and segment biological structures.

The organ detection processor 140 may comprise suitable logic, circuitry, interfaces and/or code that may be operable to analyze acquired ultrasound images to identify and segment biological structures. In various embodiments, the organ detection processor 140 may be provided as a deep neural network that may be made up of, for example, an input layer, an output layer, and one or more hidden layers in between the input and output layers. Each of the layers may be made up of a plurality of processing nodes that may be referred to as neurons. For example, the organ detection processor 140 may include an input layer having a neuron for each pixel or a group of pixels from a scan plane of an anatomical structure. The output layer may have a neuron corresponding to a plurality of pre-defined biological structures. As an example, if performing an ultrasound-based regional anesthesia procedure, the output layer may include neurons for a brachial plexus nerve bundle, the axillary artery, and the like. Other ultrasound procedures may utilize output layers that include neurons for nerves, vessels, bones, or any suitable biological structure. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the organ detection processor 140 deep neural network (e.g., convolutional neural network) may identify biological structures in ultrasound image data with a high degree of probability.

In certain embodiments, the organ detection processor 140 may be configured to identify and segment biological structures based on a user instruction via the user input device 130. For example, the organ detection processor 140 may be configured to interact with a user via the user input device 130 to receive instructions for searching the ultrasound image. As an example, a user may provide a voice command, probe gesture, button depression, or the like that instructs the organ detection processor 140 to search for a particular structure and/or to search a particular region of the ultrasound image.

The signal processor 132 may include needle detection processor 150 that comprises suitable logic, circuitry, interfaces and/or code that may be operable to analyze acquired ultrasound images to identify and segment artificial structures, such as a needle, an implantable device, or any suitable artificial structures. The needle detection processor 150 may include artificial intelligence image analysis algorithms, one or more deep neural networks (e.g., a convolutional neural network) and/or may utilize any suitable form of artificial intelligence image analysis techniques or machine learning processing functionality configured to analyze acquired ultrasound images to identify and segment artificial structures.

The needle detection processor 150 may comprise suitable logic, circuitry, interfaces and/or code that may be operable to analyze acquired ultrasound images to identify and segment artificial structures. In various embodiments, the needle detection processor 150 may be provided as a deep neural network that may be made up of, for example, an input layer, an output layer, and one or more hidden layers in between the input and output layers. Each of the layers may be made up of a plurality of processing nodes that may be referred to as neurons. For example, the needle detection processor 150 may include an input layer having a neuron for each pixel or a group of pixels from a scan plane of an anatomical structure. The output layer may have a neuron corresponding to a plurality of pre-defined artificial structures. As an example, if performing an ultrasound-based regional anesthesia procedure, the output layer may include neurons for beveled regions on anesthetic needles, and the like. Other ultrasound procedures may utilize output layers that include neurons for needles, implantable devices, or any suitable artificial structure. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the needle detection processor 150 deep neural network (e.g., convolutional neural network) may identify artificial structures in ultrasound image data with a high degree of probability.

In certain embodiments, the needle detection processor 150 may be configured to identify and segment artificial structures based on a user instruction via, the user input device 130. For example, the needle detection processor 150 may be configured to interact with a user via the user input device 130 to receive instructions for searching the ultrasound image. As an example, a user may provide a voice command, probe gesture, button depression, or the like that instructs the needle detection processor 150 to search for a particular structure and/or to search a particular region of the ultrasound image.

The signal processor 132 may include an anesthetic detection processor 160 that comprises suitable logic, circuitry, interfaces and/or code that may be operable to analyze acquired ultrasound images to identify and segment anesthetic mediums. The anesthetic detection processor 160 may include artificial intelligence image analysis algorithms, one or more deep neural networks (e.g., a convolutional neural network) and/or may utilize any suitable form of artificial intelligence image analysis techniques or machine learning processing functionality configured to analyze acquired ultrasound images to identify and segment anesthetic mediums.

The anesthetic detection processor 160 may comprise suitable logic, circuitry, interfaces and/or code that may be operable to analyze acquired ultrasound images to identify and segment anesthetic mediums. In various embodiments, the anesthetic detection processor 160 may be provided as a deep neural network that may be made up of, for example, an input layer, an output layer, and one or more hidden layers in between the input and output layers. Each of the layers may be made up of a plurality of processing nodes that may be referred to as neurons. For example, the anesthetic detection processor 160 may include an input layer having a neuron for each pixel or a group of pixels from a scan plane of an anatomical structure. The output layer may have a neuron corresponding to one or more pre-defined anesthetic mediums. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the artificial intelligence segmentation processor 140 deep neural network (e.g., convolutional neural network) may identify anesthetic mediums in ultrasound image data with a high degree of probability.

In certain embodiments, the anesthetic detection processor 160 may be configured to identify and segment anesthetic mediums based on a user instruction via the user input device 130. For example, the anesthetic detection processor 160 may be configured to interact with a user via the user input device 130 to receive instructions for searching the ultrasound image. As an example, a user may provide a voice command, probe gesture, button depression, or the like that instructs the anesthetic detection processor 160 to search for a particular anesthetic medium and/or to search a particular region of the ultrasound image.

The display and warning processor 170 may comprise suitable logic, circuitry, interfaces and/or code that may be operable to highlight and display the biological and/or artificial structures identified and segmented by the organ detection processor 140, the needle detection processor 150, and/or the anesthetic detection processor 160. For example, the display and warning processor 170 may highlight the identified and segmented structures identified by the output layer of each of the deep neural networks. The highlighting may include colorizing the pixels of the segmented structure, outlining the edges of the segmented structure, or any suitable highlighting for drawing attention to one or more structures identified and segmented by the organ detection processor 140, the needle detection processor 150, and/or the anesthetic detection processor 160. The highlighting may be overlaid on the ultrasound image and presented at the display system 134.

The display and warning processor 170 may comprise suitable logic, circuitry, interfaces and/or code that may be operable to determine distances between highlighted structures and provide a warning if the distances are smaller than a defined threshold. For example, the display and warning processor 170 may determine a distance between a needle and a nerve and may provide an alert if a head of the needle is getting too close to an epineurium of the nerve. As another example, the display and warning processor 170 may determine a distance between a needle and a vessel and may provide an alert if the needle is getting too close to the vessel. The alert may be a visual warning, audio warning, and/or physical warning. The visual warning may be a visual message presented at the display system 134, a change in the appearance of the highlighting, or any suitable visual warning. For example, the color of the highlighting (e.g., red for too close, yellow for getting close, green for not close, etc.) or the type of highlighting (e.g., colorized structure, structure outlined with solid lines, structure outlined with dashed lines, etc.) may correspond with a level of proximity between highlighted structures. As another example, the highlighting of one or more of the structures may be configured to flash if the distance between highlighted structures is less than a defined threshold. The audible warning may be an alarm, message, or any suitable audible feedback. The physical warning may include causing the probe 104 to vibrate, or any suitable physical warning.

The display and warning processor 170 may comprise suitable logic, circuitry, interfaces and/or code that may be operable to provide guidance for navigating an artificial structure to a biological structure. For example, the display and warning processor 170 may superimpose a trajectory on the ultrasound image from a highlighted needle to a highlighted nerve. In various embodiments, the display and warning processor 170 may update the trajectory as the needle is navigated to the nerve.

Figure 2:
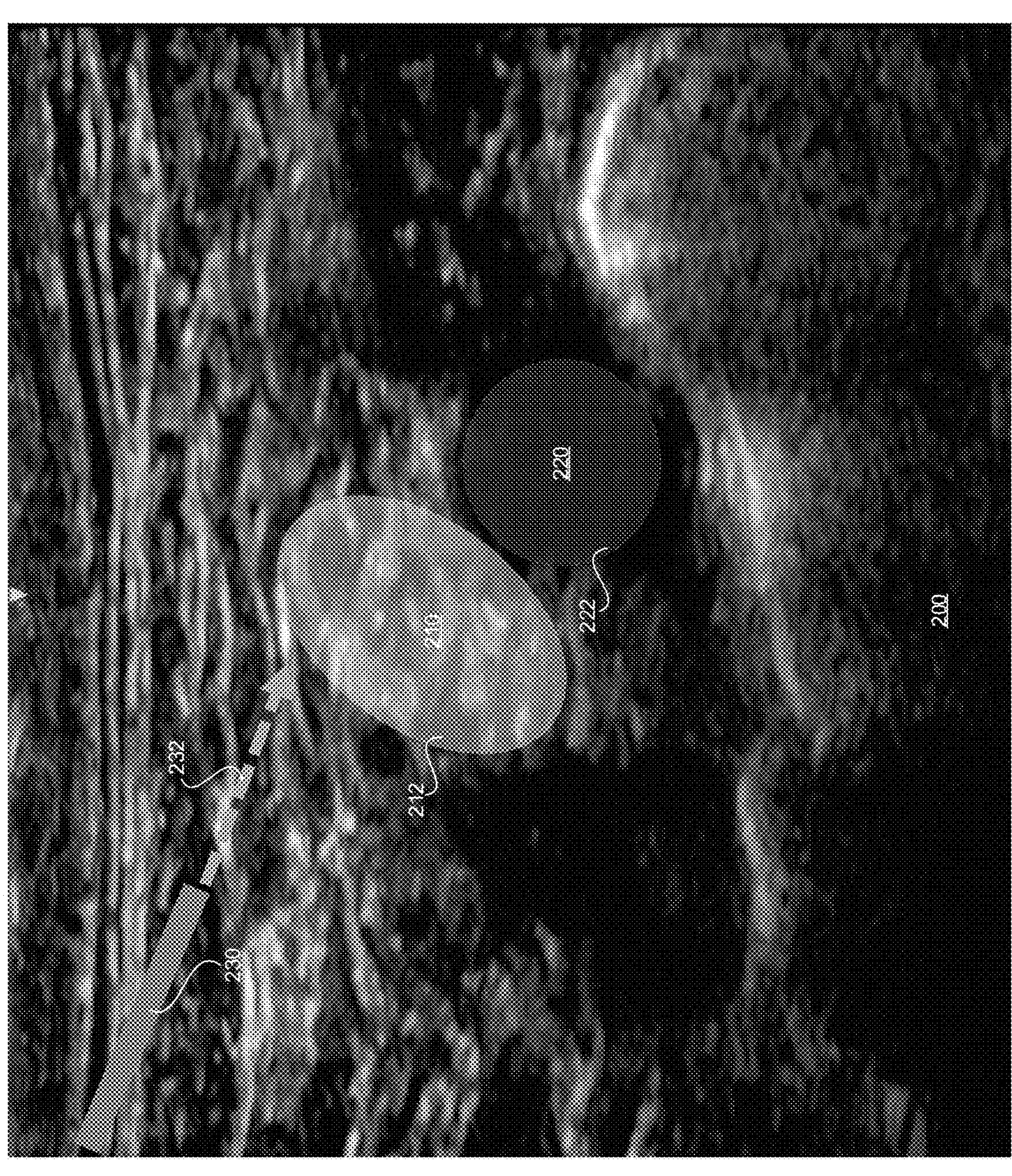
FIG. 2 is a display of an exemplary ultrasound image identifying biological and/or artificial structures to provide needle guidance, in accordance with various embodiments.

FIG. 2 is a display of an exemplary ultrasound image 200 identifying biological 210, 220 and/or artificial 230 structures to provide needle guidance 232, in accordance with various embodiments. Referring to FIG. 2, the ultrasound image 200 may comprise highlighting 212, 222, 230, provided by the display and warning processor 170, identifying structures 210, 220, 230 identified and segmented by the organ detection processor 140, the needle detection processor 150, and/or the anesthetic detection processor 160. For example, the structures may comprise a nerve 210, a vessel 220, and a needle 230. The ultrasound image 200 may comprise a trajectory 232, provided by the display and warning processor 170, to provide guidance of the needle 230 to the nerve 210.

Figure 3:
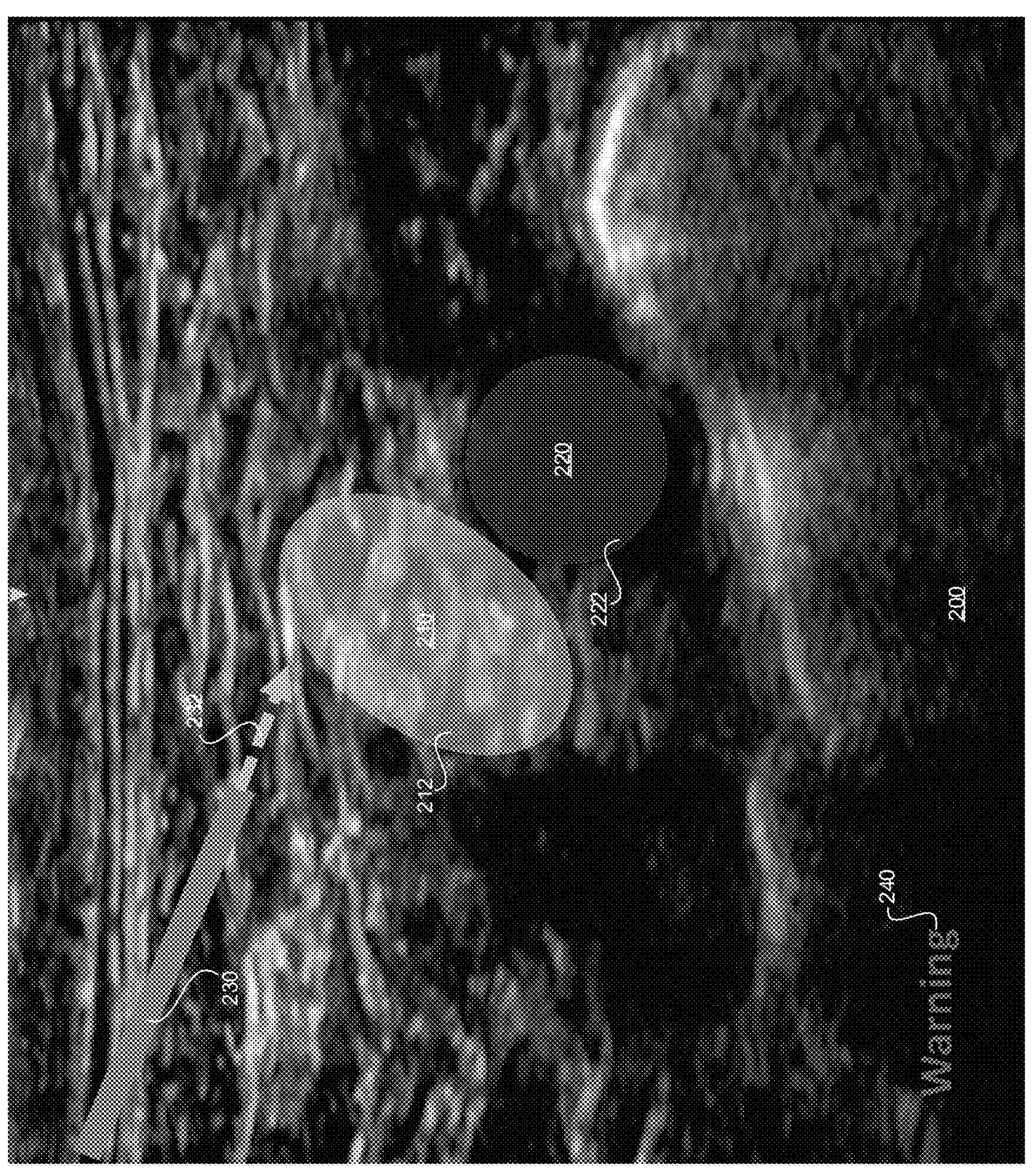
FIG. 3 is a display of an exemplary ultrasound image identifying biological and/or artificial structures to provide needle guidance and warnings, in accordance with various embodiments.

FIG. 3 is a display of an exemplary ultrasound image 200 identifying biological 210, 220 and/or artificial 230 structures to provide needle guidance 232 and warnings 240, in accordance with various embodiments. Referring to FIG. 3, the ultrasound image 200 may comprise highlighting 212, 222, 230, provided by the display and warning processor 170, identifying structures 210, 220, 230 identified and segmented by the organ detection processor 140, the needle detection processor 150, and/or the anesthetic detection processor 160. For example, the structures may comprise a nerve 210, a vessel 220, and a needle 230. The ultrasound image 200 may comprise a trajectory 232, provided by the display and warning processor 170, to provide guidance of the needle 230 to the nerve 210. The ultrasound image 200 may comprise a warning 240, provided by the display and warning processor 170, if the display and warning processor 170 determines that a distance between the needle 230 and the nerve 210 is less than a predetermined threshold, for example.

Figure 4:
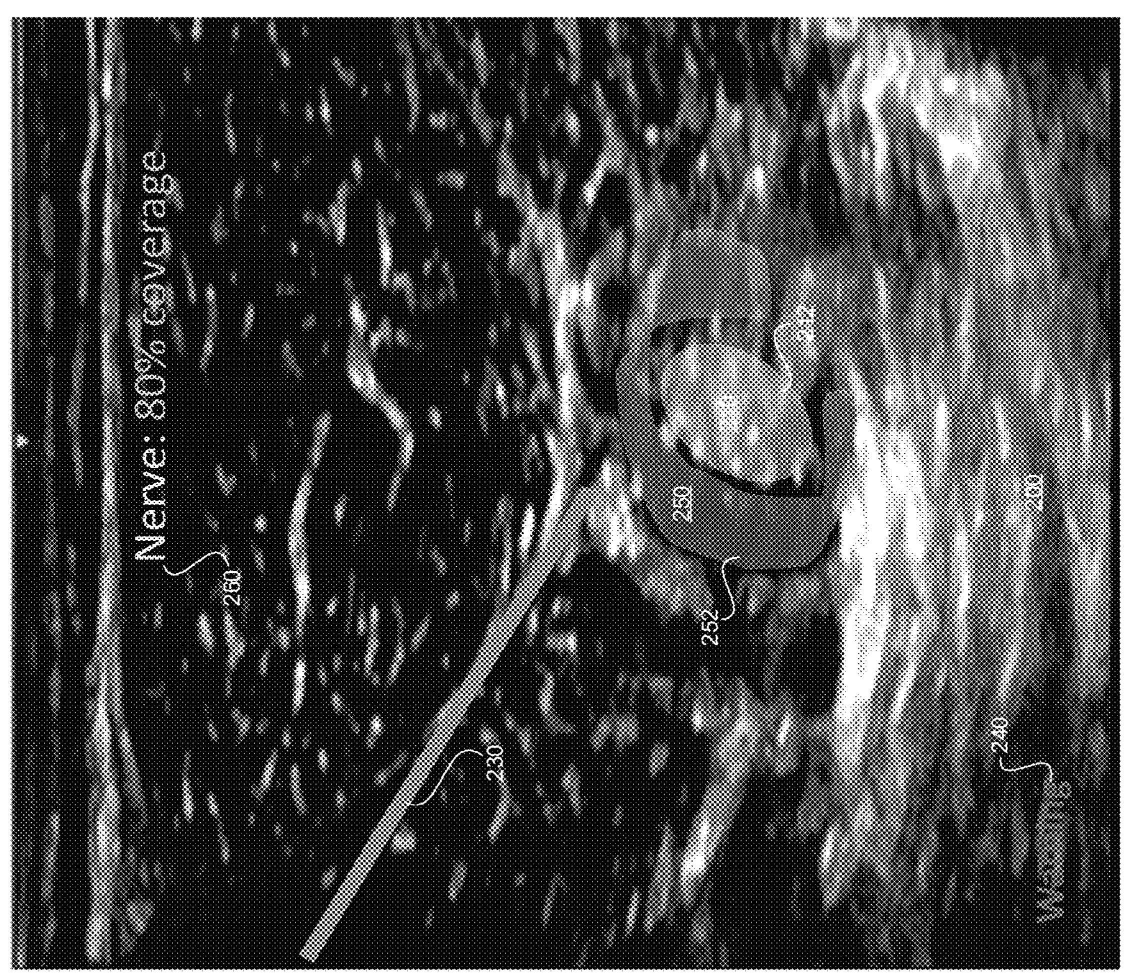
FIG. 4 is a display of an exemplary ultrasound image identifying biological and/or artificial structures to provide needle guidance, warnings, and anesthetic medium information, in accordance with various embodiments.

FIG. 4 is a display of an exemplary ultrasound image 200 identifying biological 210 and/or artificial 230, 250 structures to provide needle guidance, warnings 240, and anesthetic medium information 260, in accordance with various embodiments. Referring to FIG. 4, the ultrasound image 200 may comprise highlighting 212, 230, 252, provided by the display and warning processor 170, identifying structures 210, 230, 250 identified and segmented by the organ detection processor 140, the needle detection processor 150, and/or the anesthetic detection processor 160. For example, the structures may comprise a nerve 210, a needle 230, and an anesthetic medium 250. The ultrasound image 200 may comprise a warning 240, provided by the display and warning processor 170, if the display and warning processor 170 determines that a distance between the needle 230 and the nerve 210 is less than a predetermined threshold, for example. The ultrasound image 200 may comprise anesthetic medium information 260, provided by the display and warning processor 170, to provide information regarding a percentage of nerve coverage Referring again to FIG. 1, the display system 134 may be any device capable of communicating visual information to a user. For example, a display system 134 may include a liquid crystal display, a light emitting diode display, and/or any suitable display or displays. The display system 134 can be operable to present ultrasound images and/or any suitable information. For example, the ultrasound images presented at the display system 134 may include highlighting, trajectories, warnings, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores ultrasound image data, highlighted ultrasound images, identification instructions, segmentation instructions, highlighting instructions, and trajectory instructions, for example.

Still referring to FIG. 1, the training engine 180 may comprise suitable logic, circuitry, interfaces and/or code that may be operable to train the neurons of the deep neural network(s) of the organ detection processor 140, the needle detection processor 150, and/or the anesthetic detection processor 160. For example, the artificial organ detection processor 140, the needle detection processor 150, and/or the anesthetic detection processor 160 may be trained to automatically identify and segment biological and/or artificial structures provided in an ultrasound scan plane. For example, the training engine 180 may train the deep neural networks of the organ detection processor 140, the needle detection processor 150, and/or the anesthetic detection processor 160 using databases(s) of classified ultrasound images of various structures. As an example, the organ detection processor 140, the needle detection processor 150, and/or the anesthetic detection processor 160 may be trained by the training engine 180 with ultrasound images of particular biological and/or artificial structures to train the organ detection processor 140, the needle detection processor 150, and/or the anesthetic detection processor 160 with respect to the characteristics of the particular structure, such as the appearance of structure edges, the appearance of structure shapes based on the edges, the positions of the shapes relative to landmarks in the ultrasound image data, and the like. In an exemplary embodiment, the structures may include a brachial plexus nerve bundle, the axillary artery, beveled regions on anesthetic needles, anesthetic mediums, and/or any suitable organ, nerve, vessel, tissue, needle, implantable device, or the like. The structural information may include information regarding the edges, shapes, and positions of organs, nerves, vessels, tissue, needles, implantable devices, and/or the like. In various embodiments, the databases of training images may be stored in the archive 138 or any suitable data storage medium. In certain embodiments, the training engine 180 and/or training image databases may be external system(s) communicatively coupled via a wired or wireless connection to the ultrasound system 100.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Figure 5:
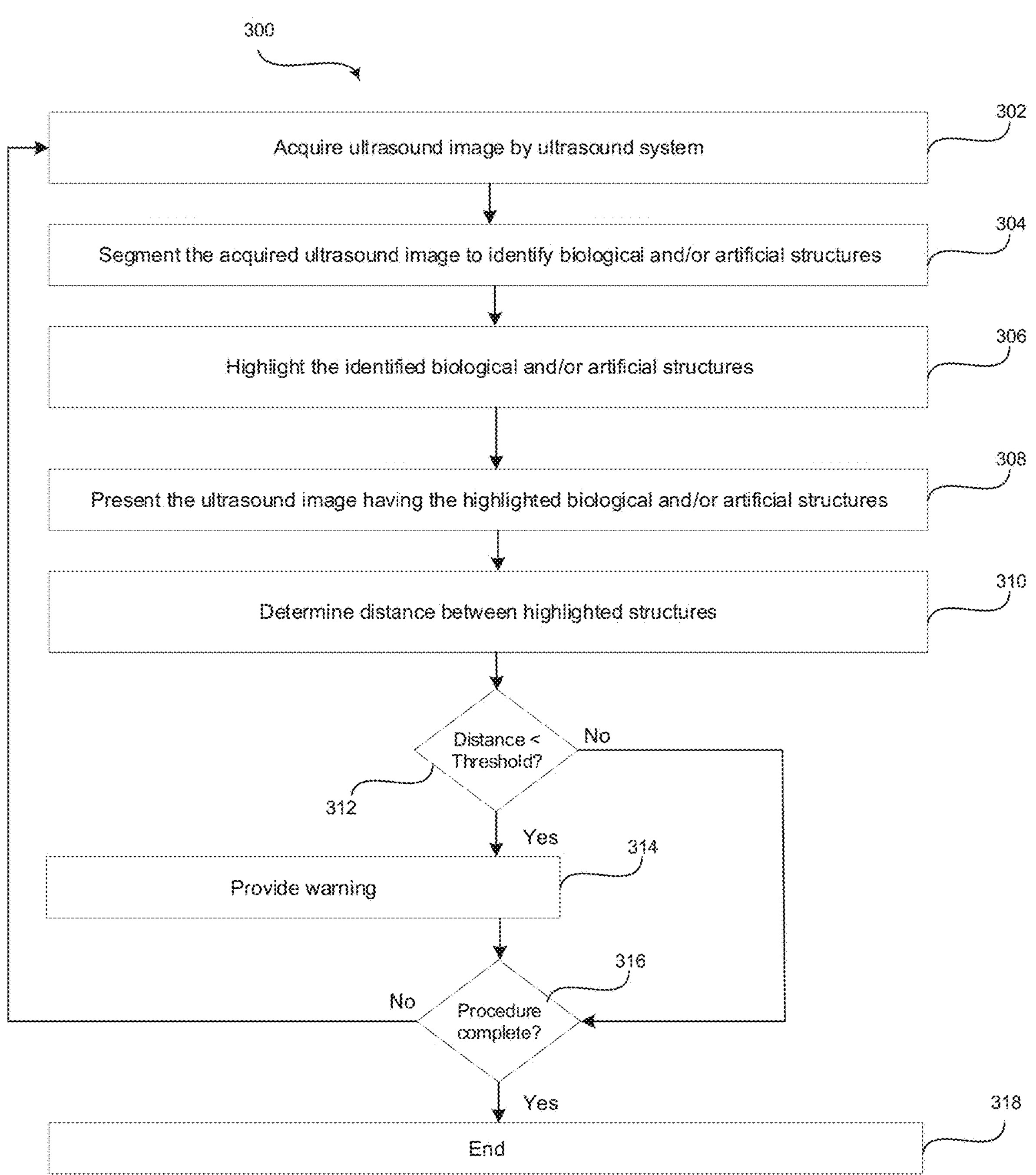
FIG. 5 is a flow chart illustrating exemplary steps that may be utilized for providing ultrasound scene analysis for needle guidance and warnings, in accordance with various embodiments.

FIG. 5 is a flow chart 300 illustrating exemplary steps 302-318 that may be utilized for providing ultrasound scene analysis for needle guidance and warnings, in accordance with various embodiments. Referring to FIG. 5, there is shown a flow chart 300 comprising exemplary steps 302 through 318. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 302, an ultrasound system 100 acquires an ultrasound image 200. For example, the ultrasound system 100 may acquire an ultrasound image 200 with an ultrasound probe 104 positioned at a scan position over region of interest.

At step 304, a signal processor 132 of the ultrasound system 100 segments the acquired ultrasound image 200 to identify biological and/or artificial structure 210, 220, 230, 250. For example, an organ detection processor 140, needle detection processor 150, and/or anesthetic detection processor 160 of the signal processor 132 may be configured to analyze the ultrasound image 200 acquired at step 302 to identify and segment biological and/or artificial structures 210, 220, 230, 250. The organ detection processor 140, the needle detection processor 150, and/or the anesthetic detection processor 160 may include artificial intelligence image analysis algorithms, one or more deep neural networks (e.g., a convolutional neural network) and/or may utilize any suitable form of artificial intelligence image analysis techniques or machine learning processing functionality configured to analyze acquired ultrasound images to identify and segment biological and/or artificial structures 210, 220, 230, 250 in the ultrasound image 200.

At step 306, a signal processor 132 of the ultrasound system 100 may highlight 212, 222, 230, 252 the biological and/or artificial structure 210, 220, 230, 250 identified at step 304. For example, a display and warning processor 170 of the signal processor 132 may be configured to highlight 212, 222, 230, 252 the identified and segmented structures 210, 220, 230, 250 identified at step 304. The highlighting 212, 222, 230, 252 may include colorizing the pixels of the segmented structure 210, 220, 230, 250, outlining the edges of the segmented structure, and/or any suitable highlight for drawing attention to one or more structures identified and segmented by the organ detection processor 140, the needle detection processor 150, and/or the anesthetic detection processor 160. In various embodiments, the highlighting of different structures 210, 220, 230 may be different colors and/or different types. The highlighting may be overlaid on the ultrasound image 200.

At step 308, the signal processor 132 of the ultrasound system 100 may present the ultrasound image 200 having the highlighted 212, 222, 230, 252 at least one biological and/or artificial structure 210, 220, 230, 250. For example, the display and warning processor 170 of the signal processor 132 may be configured to present the structure(s) 210, 220, 230, 250 (highlighted at step 306) at a display system 134 of the ultrasound system 100. In an exemplary embodiment, the display and warning processor 170 may be configured to determine and present a trajectory 232 at the display system 134 to provide guidance of the needle 230 to the nerve 210. In various embodiments, the display and warning processor 170 may be configured to present additional information with the highlighted structures 210, 220, 230, 250, such as anesthetic medium information 260 or any suitable information. As an example, the display and warning processor 170 may determine a percentage of an outer surface of a nerve 210 that is covered by anesthetic medium 250 an may present the coverage percentage 260 at the display system 134 of the ultrasound system 100.

At step 310, the signal processor 132 of the ultrasound system 100 may determine distances between highlighted structures 210, 220, 230, 150. For example, the display and warning processor 170 of the signal processor 132 may determine a distance between a needle 230 and one or both of a nerve 210 and a vessel 220.

At step 312, the signal processor 132 of the ultrasound system 100 may determine whether the calculated distance is less than a threshold. For example, the display and warning processor 170 of the signal processor 132 may determine whether the distance between a head of a needle and a nerve or a vessel is less than a threshold. The threshold may be a defined distance corresponding with a needle getting too close to the nerve or vessel. The threshold value may be user-defined or a default value. In various embodiments, the threshold may include multiple thresholds corresponding with different levels of closeness, such as not close, somewhat close, and too close. The process 300 may proceed to step 314 if the distance is less than the defined threshold or may proceed to step 316 if the distance is not less than the defined threshold.

At step 314, the signal processor 132 of the ultrasound system 100 may provide a warning if the distance is less than the threshold as determined at step 312. For example, the display and warning processor 170 of the signal processor 132 may be configured to provide an audible, visual, and/or physical warning 240 if a distance between highlighted structures 210, 220, 230, 250 is less than the threshold corresponding with the distance. As an example, the display and warning processor 170 may provide an audible message, display a visual message at display system 134, and/or facilitate vibrations at probe 104, among other things, if a distance between a needle 230 and a nerve 210 is less than a defined corresponding threshold distance.

At step 316, the signal processor 132 of the ultrasound system 100 may determine whether the ultrasound procedure is complete. For example, the signal processor 132 may determine whether the ultrasound system 100 is acquiring ultrasound images 200 and/or detecting biological and/or artificial structures 210, 220, 230, 250 in acquired ultrasound images 200. The process 300 may return to step 302 to continue acquiring ultrasound images 200 if the signal processor 132 determines that the procedure is not yet complete. The process 300 may proceed to step 318 if the signal processor 132 determines that the procedure is finished.

At step 318, the process 300 may end when the ultrasound procedure is finished.

Aspects of the present disclosure provide a method 300 and system 100 for analyzing ultrasound scenes to provide needle guidance and warnings. In accordance with various embodiments, the method 300 may comprise acquiring 302, by an ultrasound system 100, an ultrasound image 200. The method 300 may comprise segmenting 304, by at least one processor 132, 140, 150, 160, the ultrasound image to identify a plurality of structures 210, 220, 230, 250 in the ultrasound image 200. The method 400 may comprise highlighting 306, by the at least one processor 132, 170, the plurality of structures 210, 220, 230, 250 in the ultrasound image 200 to create a highlighted ultrasound image 200. The method 300 may comprise presenting 308, by the at least one processor 132, 170, the highlighted ultrasound image 200 at a display system 134. The method 300 may comprise determining 310, by the at least one processor 132, 170, a distance between at least two of the plurality of structures 210, 220, 230, 250 in the ultrasound image 200. The method 300 may comprise providing 314, by the at least one processor 132, 170, a warning 240 if the distance between the at least two of the plurality of structures 210, 220, 230, 250 in the ultrasound image 200 is less than a threshold.

In an exemplary embodiment, the plurality of structures 210, 220, 230, 250 may comprise at least one biological structure 210, 220 and at least one artificial structure 230, 250. In a representative embodiment, the at least one biological structure 210, 220 comprises one or both of a nerve 210 and a vessel 220. In various embodiments, the at least one artificial structure 230, 250 comprises one or both of a needle 230 and an anesthetic medium 250. In certain embodiments, the highlighting 212, 222, 230, 252 may comprise one or more of colorizing pixels 212, 222, 252 of one or more of the plurality of structures 210, 220, 230, 250, outlining edges of the one or more of the plurality of structures 210, 220, 230, 250, and overlaying an identifier 230 on the one or more of the plurality of structures 210, 220, 230, 250. In an exemplary embodiment, the plurality of structures 210, 220, 230, 250 comprises a needle 230 and a nerve 210. The method 300 may comprise superimposing 308, by the at least one processor 132, 170, a trajectory 232 from the needle 230 to the nerve 210 on the ultrasound image 200 presented at the display system 134. In a representative embodiment, the plurality of structures 210, 220, 230, 250 comprises an anesthetic medium 250 and a nerve 210. The method 300 may comprise determining 308, by the at least one processor 132, 170, a percent coverage 260 of the nerve 210 by the anesthetic medium 250. The method 300 may comprise presenting 308, by the at least one processor 132, 170, the percent coverage 260 at the display system 134. In certain embodiments, the warning 240 is one or more of an audio warning, a visual warning 240, and a physical warning.

Various embodiments provide a system 100 for analyzing ultrasound scenes to provide needle guidance and warnings. The system 100 may comprise an ultrasound system 100, at least one processor 132, 140, 150, 160, 170, and a display system 134. The ultrasound system 100 may be configured to acquire an ultrasound image 200. The at least one processor 132, 140, 150, 160 may be configured to segment the ultrasound image 200 to identify a plurality of structures 210, 220, 230, 250 in the ultrasound image 200. The at least one processor 132, 170 may be configured to highlight 212, 222, 230, 252 the plurality of structures 210, 220, 230, 250 in the ultrasound image 200 to create a highlighted ultrasound image 200. The at least one processor 132, 170 may be configured to present the highlighted ultrasound image 200 at a display system 134. The at least one processor 132, 170 may be configured to determine a distance between at least two of the plurality of structures 210, 220, 230, 250 in the ultrasound image 200. The at least one processor 132, 170 may be configured to provide a warning 240 if the distance between the at least two of the plurality of structures 210, 220, 230, 250 in the ultrasound image 200 is less than a threshold. The display system 134 may be configured to display the highlighted ultrasound image 200.

In a representative embodiment, the plurality of structures 210, 220, 230, 250 comprises at least one biological structure 210, 220 and at least one artificial structure 230, 250. In various embodiments, the at least one biological structure 210, 220 may comprise one or both of a nerve 210 and a vessel 220. The at least one artificial structure 230, 150 may comprise one or both of a needle 230 and an anesthetic medium 250. In certain embodiments, the highlight 212, 222, 230, 252 comprises one or more of colorized pixels 212, 222, 252 of one or more of the plurality of structures 210, 220, 230, 250, outlined edges of the one or more of the plurality of structures 210, 220, 230, 250, and an identifier 230 overlaid on the one or more of the plurality of structures 210, 220, 230, 250. In an exemplary embodiment, the plurality of structures 210, 220, 230, 250 may comprise a needle 230 and a nerve 210. The at least one processor 132, 170 may be configured to present a trajectory 232 from the needle 230 to the nerve 210 overlaid on the ultrasound image 200 at the display system 134. In a representative embodiment, the plurality of structures 210, 220, 230, 250 may comprise an anesthetic medium 250 and a nerve 210. The at least one processor 132, 170 may be configured to determine a percent coverage 260 of the nerve 210 by the anesthetic medium 250. The at least one processor 132, 170 may be configured to present the percent coverage 260 at the display system 134. In various embodiments, the warning 240 may be one or more of an audio warning, a visual warning 240, and a physical warning.

Certain embodiments provide a non-transitory computer readable medium having stored thereon, a computer program having at least one code section. The at least one code section is executable by a machine for causing the machine to perform steps 300. The steps 300 may comprise receiving 302 an ultrasound image 200. The steps 300 may comprise segmenting 304 the ultrasound image 200 to identify a plurality of structures 210, 220, 230, 250 in the ultrasound image 200. The steps 300 may comprise highlighting 306 the plurality of structures 210, 220, 230, 250 in the ultrasound image 200 to create a highlighted ultrasound image 200. The steps 300 may comprise presenting 308 the highlighted ultrasound image 200 at a display system 134. The steps 300 may comprise determining 310 a distance between at least two of the plurality of structures 210, 220, 230, 250 in the ultrasound image 200. The steps 300 may comprise providing 314 a warning 240 if the distance between the at least two of the plurality of structures 210, 220, 230, 250 in the ultrasound image 200 is less than a threshold.

In various embodiments, the plurality of structures 210, 220, 230, 250 may comprise at least one biological structure 210, 220 and at least one artificial structure 230, 250. The at least one biological structure 210, 220 may comprise one or both of a nerve 210 and a vessel 220. The at least one artificial structure 230, 250 may comprise one or both of a needle 230 and an anesthetic medium 250. In certain embodiments, the highlighting 212, 222, 230, 252 may comprise one or more of colorizing pixels 212, 222, 252 of one or more of the plurality of structures 210, 220, 230, 250, outlining edges of the one or more of the plurality of structures 210, 220, 230, 250, and overlaying an identifier 230 on the one or more of the plurality of structures 210, 220, 230, 250. In an exemplary embodiment, the plurality of structures 210, 220, 230, 250 may comprise a needle 230 and a nerve 210. The steps 300 may comprise superimposing 308 a trajectory 232 from the needle 230 to the nerve 210 on the ultrasound image 200 presented at the display system 134. In a representative embodiment, the warning 240 may be one or more of an audio warning, a visual warning 240, and a physical warning.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing ultrasound scene analysis for needle guidance and warnings.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method for providing needle guidance and location-based warnings during a guided ultrasound-based regional anesthesia procedure, the method comprising:

acquiring, by an ultrasound system, an ultrasound image depicting at least one artificial structure and at least one biological structure, the at least one biological structure comprising a nerve designated for regional anesthesia treatment, the at least one artificial structure comprising a needle being navigated to the nerve, the needle operable to administer an amount of anesthetic medium to the nerve during the ultrasound-based regional anesthesia procedure;

segmenting, by at least one processor, the ultrasound image to identify a plurality of structures in the ultrasound image, wherein the plurality of structures comprises the at least one artificial structure and the at least one biological structure;

highlighting, by the at least one processor, the plurality of structures segmented in the ultrasound image to create a highlighted ultrasound image;

presenting, by the at least one processor, the highlighted ultrasound image at a display system;

superimposing, by the at least one processor, a trajectory from the needle to the nerve designated for regional anesthesia treatment on the ultrasound image presented at the display system to provide the needle guidance, wherein the trajectory is updated as the needle is navigated to the nerve;

determining, by the at least one processor, a distance between the needle and the at least one biological structure highlighted in the ultrasound image is less than a threshold; and providing, by the at least one processor, a location-based warning in response to the determining the distance between the needle and the at least on biological structure highlighted in the ultrasound image is less than the threshold.

2. The method of claim 1, wherein the threshold comprises a plurality of thresholds, each of the plurality of thresholds corresponding with a different distance associated with a different level of closeness.

3. The method of claim 1, wherein the at least one biological structure further comprises a vessel.

4. The method of claim 1, wherein the at least one artificial structure further comprises the anesthetic medium.

5. The method of claim 1, wherein the highlighting comprises one or more of:

colorizing pixels of one or more of the plurality of structures, outlining edges of the one or more of the plurality of structures, and overlaying an identifier on the one or more of the plurality of structures.

6. The method of claim 1, wherein the highlighting distinguishes between different levels of proximity between the needle and the at least one biological structure by:

a color of the highlighting; and/or a type of highlighting.

7. The method of claim 1, wherein the at least one artificial structure further comprises an anesthetic medium, and comprising:

determining, by the at least one processor, a percent coverage of the nerve by the anesthetic medium, and presenting, by the at least one processor, the percent coverage at the display system.

8. The method of claim 1, wherein the location-based warning is one or more of an audio warning, a visual warning, and a physical warning.

9. A system configured to provide needle guidance and location-based warnings during a guided ultrasound-based regional anesthesia procedure, the system comprising:

an ultrasound system configured to acquire an ultrasound image depicting at least one artificial structure and at least one biological structure, the at least one biological structure comprising a nerve designated for regional anesthesia treatment, the at least one artificial structure comprising a needle being navigated to the nerve, the needle operable to administer an amount of anesthetic medium to the nerve during the ultrasound-based regional anesthesia procedure;

at least one processor configured to:

segment the ultrasound image to identify a plurality of structures in the ultrasound image, wherein the plurality of structures comprises the at least one artificial structure and the at least one biological structure;

highlight the plurality of structures segmented in the ultrasound image to create a highlighted ultrasound image;

present the highlighted ultrasound image at a display system;

superimpose a trajectory from the needle to the nerve designated for regional anesthesia treatment on the ultrasound image presented at the display system to provide the needle guidance, wherein the trajectory is updated as the needle is navigated to the nerve;

determine a distance between the needle and the at least one biological structure highlighted in the ultrasound image is less than a threshold; and provide a location-based warning in response to the distance between the at least two of the needle and the at least on biological structure highlighted in the ultrasound image determined to be less than the threshold; and the display system configured to display the highlighted ultrasound image.

10. The system of claim 9, wherein the threshold comprises a plurality of thresholds, each of the plurality of thresholds corresponding with a different distance associated with a different level of closeness.

11. The system of claim 9, wherein:

the at least one biological structure further comprises a vessel, and/or the at least one artificial structure further comprises the anesthetic medium.

12. The system of claim 9, wherein the highlight comprises one or more of:

colorized pixels of one or more of the plurality of structures, outlined edges of the one or more of the plurality of structures, and an identifier overlaid on the one or more of the plurality of structures.

13. The system of claim 9, wherein the threshold comprises a plurality of thresholds, each of the plurality of thresholds corresponding with a different distance associated with a different level of closeness.

14. The system of claim 9, wherein:

the at least one artificial structure further comprises the anesthetic medium, the at least one processor is configured to determine a percent coverage of the nerve by the anesthetic medium, and the at least one processor is configured to present the percent coverage at the display system.

15. The system of claim 9, wherein the location-based warning is one or more of an audio warning, a visual warning, and a physical warning.

16. A non-transitory computer readable medium having stored thereon, a computer program having at least one code section, the at least one code section being executable by a machine for causing the machine to perform steps comprising:

receiving an ultrasound image depicting at least one artificial structure and at least one biological structure, the at least one biological structure comprising a nerve designated for regional anesthesia treatment, the at least one artificial structure comprising a needle being navigated to the nerve, the needle operable to administer an amount of anesthetic medium to the nerve during an ultrasound-based regional anesthesia procedure;

segmenting the ultrasound image to identify a plurality of structures in the ultrasound image, wherein the plurality of structures comprises the at least one artificial structure and the at least one biological structure;

highlighting the plurality of structures segmented in the ultrasound image to create a highlighted ultrasound image;

presenting the highlighted ultrasound image at a display system;

superimposing a trajectory from the needle to the nerve designated for regional anesthesia treatment on the ultrasound image presented at the display system to provide needle guidance, wherein the trajectory is updated as the needle is navigated to the nerve;

determining a distance between the needle and the at least one biological structure highlighted in the ultrasound image is less than a threshold; and providing a location-based warning in response to the determining the distance between the needle and the at least on biological structure highlighted in the ultrasound image is less than the threshold.

17. The non-transitory computer readable medium of claim 16, wherein:

the at least one biological structure further comprises a vessel, and/or the at least one artificial structure further comprises the anesthetic medium.

18. The non-transitory computer readable medium of claim 16, wherein the highlighting comprises one or more of:

colorizing pixels of one or more of the plurality of structures, outlining edges of the one or more of the plurality of structures, and overlaying an identifier on the one or more of the plurality of structures.

19. The non-transitory computer readable medium of claim 16, wherein the at least one artificial structure further comprises an anesthetic medium, and comprising:

determining a percent coverage of the nerve by the anesthetic medium, and presenting the percent coverage at the display system.

20. The non-transitory computer readable medium of claim 16, wherein the location-based warning is one or more of an audio warning, a visual warning, and a physical warning.

* * * * *